United States Patent
Schürenberg et al.

(10) Patent No.: US 10,546,739 B2
(45) Date of Patent: Jan. 28, 2020

(54) DISPENSER SYSTEM FOR MASS SPECTROMETRIC SAMPLE PREPARATIONS

(71) Applicant: Bruker Daltonik GmbH, Bremen (DE)

(72) Inventors: Martin Schürenberg, Tarmstedt (DE); Alexander Vossgröne, Bremen (DE)

(*) Notice: Subject to any disclaimer, the term of this patent is extended or adjusted under 35 U.S.C. 154(b) by 0 days.

(21) Appl. No.: 16/121,053

(22) Filed: Sep. 4, 2018

(65) Prior Publication Data

US 2018/0374692 A1  Dec. 27, 2018

Related U.S. Application Data

(63) Continuation of application No. 14/483,223, filed on Sep. 11, 2014, now Pat. No. 10,103,017.

(30) Foreign Application Priority Data

Sep. 13, 2013  (EP) .................................. 13004465

(51) Int. Cl.
| | |
|---|---|
| *H01J 49/04* | (2006.01) |
| *B01L 3/02* | (2006.01) |
| *G01N 35/10* | (2006.01) |
| *H01J 49/26* | (2006.01) |

(52) U.S. Cl.
CPC .......... *H01J 49/0431* (2013.01); *B01L 3/021* (2013.01); *B01L 3/0241* (2013.01); *G01N 35/1004* (2013.01); *H01J 49/0418* (2013.01); *H01J 49/26* (2013.01); *B01L 2200/0615* (2013.01); *B01L 2300/0654* (2013.01)

(58) Field of Classification Search
CPC .... H01J 49/0418; H01J 49/0431; H01J 49/26; B01L 3/021; B01L 3/0241; B01L 2300/0654; B01L 2200/0615; G01N 35/1004

See application file for complete search history.

(56) References Cited

U.S. PATENT DOCUMENTS

| | | | | |
|---|---|---|---|---|
| 4,574,850 | A | * | 3/1986 | Davis ..................... G01N 35/10 141/9 |
| 5,601,980 | A | * | 2/1997 | Gordon ................. B01L 3/0262 422/547 |
| 6,713,021 | B1 | * | 3/2004 | Shvets .................. B01L 3/0265 137/487.5 |

(Continued)

*Primary Examiner* — Benjamin L Osterhout
(74) *Attorney, Agent, or Firm* — Benoit & Côté Inc.

(57) ABSTRACT

The invention relates to the preparation of samples on mass spectrometric sample supports with dispensing of liquids, and particularly to devices and methods to clean the dispenser. During dispensing of hundreds of samples, solved material may crystallize over time as deposit at the capillary tip of the dispenser, which impedes the vertical detachment of the drop in the medium and long run. Therefore, frequently cleaning the capillary tip is essential for a robust operation of the preparation device. The invention proposes to automatically clean the dispenser tip by creating a drop of washing fluid, such as pure solvent, fully enclosing the dispenser tip. The washing fluid is fed through a channel outside the central dispenser capillary to a location slightly above the capillary tip. The size of the hanging drop of washing fluid is photometrically regulated and monitored to prevent it from falling off prematurely.

19 Claims, 4 Drawing Sheets

(56) References Cited

U.S. PATENT DOCUMENTS

| | | | | |
|---|---|---|---|---|
| 6,744,046 B2* | 6/2004 | Valaskovic | ........... | H01J 49/165 239/3 |
| 2002/0168297 A1* | 11/2002 | Shvets | ................... | B01L 3/021 422/400 |
| 2003/0049863 A1* | 3/2003 | Woodward | ............ | B01L 3/0262 436/180 |
| 2005/0223814 A1* | 10/2005 | Shvets | .................. | B01L 3/0241 73/861.08 |
| 2005/0244303 A1* | 11/2005 | Ingenhoven | ............ | B01L 3/021 422/511 |
| 2006/0258011 A1* | 11/2006 | Shvets | ............... | G01N 35/1004 436/49 |
| 2007/0039866 A1* | 2/2007 | Schroeder | ........ | G01N 27/44769 210/265 |
| 2007/0187437 A1* | 8/2007 | Lord | ................. | B65D 83/0005 222/568 |
| 2008/0023028 A1* | 1/2008 | Fujita | ................... | B08B 7/0035 134/1.1 |
| 2008/0048664 A1* | 2/2008 | Iwata | .................... | G01N 30/84 324/469 |
| 2012/0143152 A1* | 6/2012 | Hunter | ................. | A61B 5/0059 604/298 |

\* cited by examiner

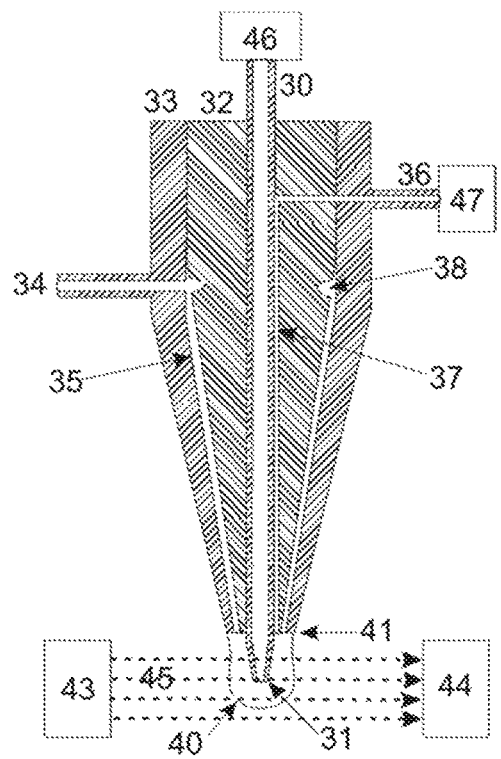
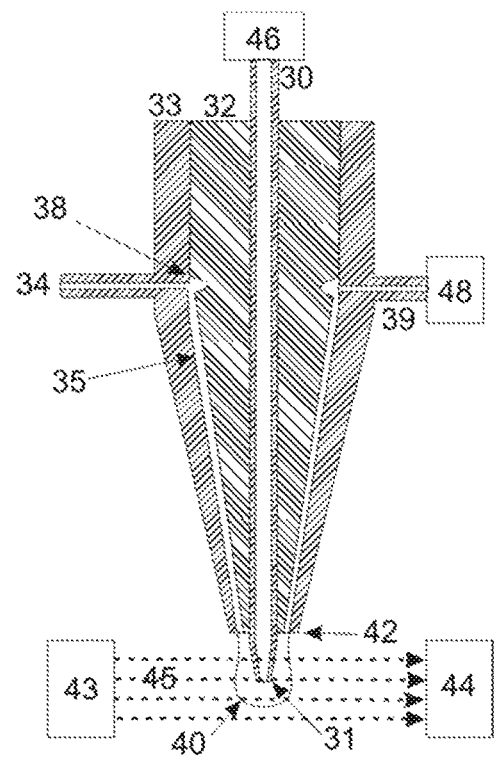
FIGURE 4A    FIGURE 4B
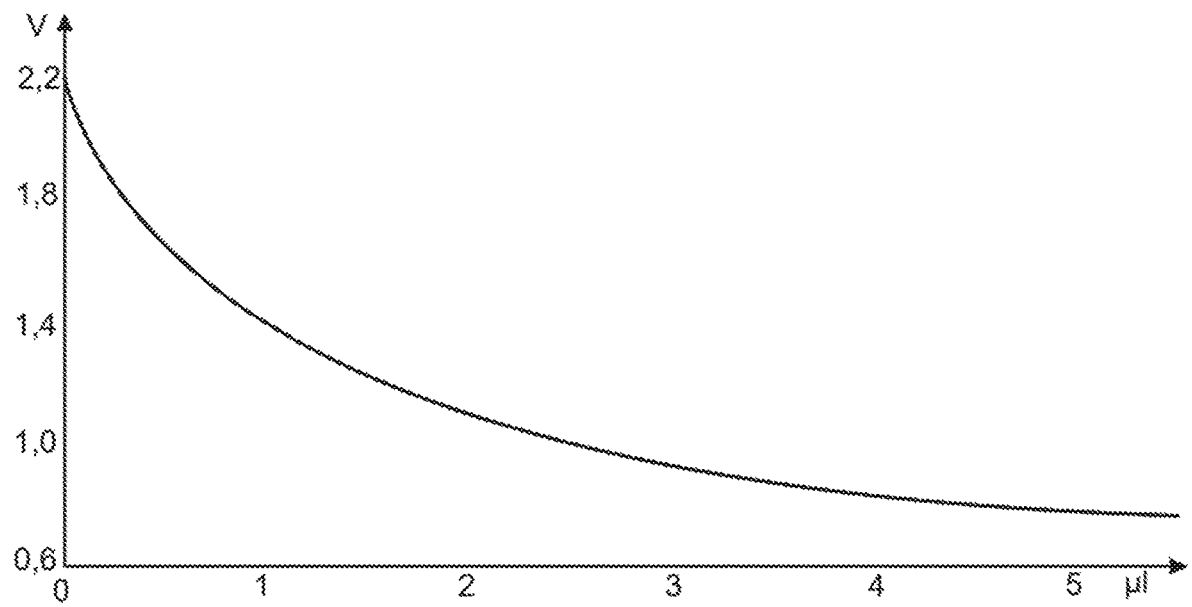
FIGURE 5

DISPENSER SYSTEM FOR MASS SPECTROMETRIC SAMPLE PREPARATIONS

BACKGROUND OF THE INVENTION

Field of the Invention

The invention relates to the preparation of samples on mass spectrometric sample supports with dispensing of liquids, and particularly to devices and methods to clean the dispenser.

Description of the Related Art

The preparation of samples for ionization by matrix-assisted laser desorption (MALDI) or similar ionization methods requires the use of organic solvents to apply the solution containing matrix material onto the individual samples under analysis. These samples have to be applied to the sample support manually or with the aid of pipetting robots. The solvents must subsequently be vaporized in order to allow crystals of the matrix substance, into which the analyte substances have to be embedded, to grow. Since ionization by matrix-assisted laser desorption (MALDI) and its requirements are widely known, no detailed description will be given here.

Today, ionization by matrix-assisted laser desorption is used widely for the mass spectrometric identification of microbes. This identification of microbial samples involves the daily preparation of hundreds of thousands of samples in many hundreds of microbiological laboratories. The preparation of microbes should serve here as an example of sample preparation.

Since only the substances from inside the microbe cells are usable for the mass spectrometric identification, the microbe cells must first be cell disrupted. This cell disruption also takes place predominantly on the sample support. The first step is to apply small, hardly visible quantities of around $10^5$ to $10^7$ microbes from agar plate colonies onto the test sites of the sample support. This transfer of microbes is widely done manually, but there are automatic devices available for this purpose. The cells of the microbes are usually cell disrupted on the sample support by strong acids, which must subsequently be dried up by vaporization. The acids used for this purpose are 70-percent formic acid (boiling point 101° C.; vapor pressure 43 hPa at 20° C.) or trifluoroacetic acid of similar concentration (TFA; boiling point 72° C.; vapor pressure 110 hPa at 20° C.). Quantities of around one microliter are applied onto each sample. When they have dried, the matrix solution is applied, also in quantities of around one microliter. The matrix solution usually contains a solid organic acid (usually α-cyano-4-hydroxycinnamic acid, HCCA, but also 2,5-dihydroxybenzoic acid, DHB, for example) in a solvent mixture of acetonitrile and alcohols. For reasons of occupational health and safety, ethanol is usually used, although methanol would be the better alternative. If the cell walls have not yet been completely destroyed by the acid, the matrix solution penetrates into the microbes through the weakened cell walls and causes them to burst by osmosis. Soluble contents, in particular the soluble proteins, then dissolve in the matrix solution. The drying of the matrix solution causes tiny crystals of matrix substance to form, into whose crystal lattice or crystal boundaries molecules of the contents are embedded. The microbes are then identified with the aid of a mass spectrum of the contents.

The sample supports are usually the size of microtitration plates (or a fraction thereof) and nowadays usually have 48, 96 or 384 visible test sites for the application and preparation of the samples. Sample supports with 1536 test sites are also in use. The test sites with diameters of 0.8 to 3.0 millimeters can be identified in some embodiments with the aid of milled-in rings, whose sharp milled edges prevent the applied acids and solvents from flowing laterally away. The test sites can also take the form of hydrophilic areas in a hydrophobic environment.

The sample support can especially also contain small pins, around 2 millimeters in diameter, which are inset into the sample support so as to be flush with the surface. The pins can be individually loaded with microbes by direct contact with microcolonies on agar surfaces. This can greatly shorten the culturing times, as is disclosed in the patent application WO 2013/182648 A1 assigned to the Applicant. The holes for the pins can have a slight chamfer, which keeps the edges of the pins clear so that the surface tension of the liquid applied to the end of the pins prevents it from running over the edge of the pins.

At present, the preparation is largely carried out manually with dispensing pipettes, without a hood, because hoods are rare in microbiological laboratories. This can be a health hazard if the ventilation is insufficient. Even when a hood is available, it is often not used because accurate pipetting onto a small sample spot in an open hood is very awkward. So, devices for automatic preparation which automate the application of the acids and the matrix solutions, and preferably do not release hazardous vapors so that a hood is not required, are desirable.

Liquids in quantities of around one microliter do not drip by their own weight even from very fine pipette tips, but are applied according to the prior art by dabbing them onto the sample. A new pipette tip must be used for each sample in order to prevent samples being transferred. Non-contact application of the liquids onto the samples is particularly advantageous because it eliminates the need to replace the pipette tips each time.

The generation of free-flying droplets with volumes of only a few nanoliters is known particularly from printing technology; some systems operate with piezo technology, others with vapor-bubble technology. With this technology, the droplets are ejected from nozzles. This technology does not lend itself to the application described here because almost a thousand tiny droplets, whose surface area is large relative to their volume, would have to be applied to a test site, preferably without any evaporation at all. Since matrix solutions near the saturation limit have to be used, there is a risk that deposits will form on the nozzle outlets at an early stage, meaning that the drops no longer leave the nozzle in the correct direction, and that the matrix solution will crystallize out prematurely in the flying droplets.

Dispensers which apply liquids with volumes of around one microliter onto test sites positioned below the dispenser, and which operate with falling drops of correct size without direct contact of the dispenser tip to the sample site, are also known in principle and can be used here. For this type of non-contact application, it is necessary to position the dispenser exactly vertically above the test site (or the test site on the sample support vertically below the dispenser). For the dispensing of these small quantities of liquid onto the test sites, there are different technical solutions, such as detaching the drop by pressure surges in the liquid feed, acoustic shock waves generated by piezo crystals, or sudden vertical movement of the capillary tip. Particularly simple and low-cost is a dispenser unit which has outer gas channels, arranged symmetrically around the central capillary and pointing to the tip of the central capillary. There may be a single annular channel by a concentric capillary around the dispensing capillary, or there may be an arrangement of at least two, preferably three or four single channels. A tiny pump presses a drop of around one microliter out of the central capillary; a small pressure surge of air or other suitable gas through the surrounding gas channel(s) then strips the hanging drop of dispensing liquid from the central capillary and causes it to fall vertically onto the test site. A simple arrangement is shown in FIG. 1, showing two concentric capillaries, the inner for the dispensing liquid, the outer for the gas surge. The pressure surge of the gas, the height of the fall and the fall speed of the droplet must be small enough so that the drop does not splatter, but large enough so that the drop does not simply roll away on the sample surface. The non-contact deposition of the liquid drops means that replaceable pipette tips are no longer required for the preparation.

Because quite often matrix solutions near saturation have to be used to prepare the samples for a mass spectrometric analysis, the function of the dispenser is repeatedly disturbed by crystals of matrix material formed and growing at the tip of the dispenser over time. Quite often wet crystals form at the outside (or outer circumference) of the tip, creeping slowly upwards at one side of the tip during subsequent dispensing cycles. When such obstruction exists, there is a danger that the drop of dispensing liquid, prior to being detached, is drawn upwards at one side of the tip by the easy wettability of the deposit in contrast to the commonly low wettability of the tip material. As a consequence, the drop stripped off by the gas surge will not fall just vertically and eventually could miss the sample site on the sample support. According to the prior art, the dispenser has to be dismounted and cleaned frequently; for that purpose, at least the inner capillary has to be emptied, then filled with washing fluid (in most cases a pure liquid solvent). The tip has to be washed by rinsing inside and outside. Then the washing fluid is removed from the tip, and dispensing fluid has to be refilled.

Dispensers can be equipped with drop size regulation systems, likewise known since long (see, for instance, publication JP 1986-231461; Apr. 5, 1985; F. Sugaya, describing a photometric drop size measuring and regulating system; also U.S. Pat. No. 5,601,980 A or US 2006/0144331 A1).

The present disclosure references ionization by matrix-assisted laser desorption (MALDI), where ions are produced during the desorption by pulsed laser beams. It goes without saying that sample preparations for other types of ionization shall also be possible where, for example, the analyte substances in the prepared samples are first transferred into the gaseous phase, and only then ionized. Simple laser desorption in combination with chemical ionization (LDCI) can be carried out, for example, as can direct electrospray ionization from the surface (DESI), but other types of ionization can also be used. Accordingly, the term "ionization with matrix-assisted laser desorption" must not be understood as a restriction.

SUMMARY OF THE INVENTION

The invention provides devices and automatic methods for cleaning dispensers without having to dismount the dispenser or even to remove the dispensing liquid from the dispenser capillary. The dispensers according to the invention do not need to comprise any moving parts other than micropumps for the cleaning process, preferably inexpensive peristaltic micropumps. The cleaning process can be started any time, for instance periodically, or each time after the preparation of all samples of a support plate with a certain number of sample sites, such as 384. Frequent cleaning is essential for a robust operation of the dispenser because dispensing solutions near saturation easily form deposits near the tip of the dispenser.

The invention can use dispensers which are known as such, where a drop of suitable size is pressed out from a capillary tip with a micropump, and is detached by any chosen process, for example by a pressure surge of a surrounding gas flow, in such a way that it falls vertically onto the sample site on the sample support.

The invention proposes to feed a washing fluid for dissolving the deposit not through the inner capillary of the dispenser, but through one or more outer channels to a location at the outer wall of the inner capillary a short distance above the tip, forming a drop completely enclosing the tip, particularly its outside surface. As an example, one or all of the gas channels may be used to create this drop of washing fluid around the tip of the dispensing capillary (if the means to release the drop comprises gas channels), but it is also possible to use an extra channel (or several extra channels), which ends at or near the outer wall of the capillary (slightly) above the tip. This makes it possible to carry out the cleaning without having to change the liquid in the inner dispensing capillary, which accelerates and simplifies the cleaning process in general.

The invention is particularly applicable for dispensers comprising an optical device with light source and light detector to monitor and regulate the size of each individual hanging drop before it is detached. With these devices, it is not only possible to regulate the drop of dispensing liquid, but also the drop of washing fluid. It has been found advantageous to form a relatively large drop of liquid solvent as the washing fluid around the capillary tip, with a volume of about four to eight microliters, and to keep this drop in motion by, preferably repeatedly, drawing a part of the washing fluid into the inner capillary and pressing it out again with the dispensing micropump, particularly to clean the interior of the tip. This motion helps to dissolve the deposit but requires monitoring the drop size to prevent the drop from falling off prematurely. The drop of washing fluid can subsequently be dropped into a waste shaft. If required, this cleaning cycle can be repeated with new drops of washing fluid several times, before the dispensing is resumed. The washing fluid can be pumped through the gas channels or the extra channel(s) to the outer surface of the dispenser tip by a further micropump.

The quantities of liquid to be dispensed regularly onto the sample site amount to only 0.5 to 1.5 microliters, and form droplets around 1.0 to 1.4 millimeters in diameter. For the washing process, a larger drop volume of about four to eight microliters has proven to be favorable, with a diameter of about 2.0 to 2.7 millimeters. In contrast to a drop of dispensing liquid which is pressed out, and then is pendant directly and only from the tip of the central dispensing capillary, this drop of washing fluid should hang from a location (slightly) above the tip, enclosing completely the outside of the dispenser tip. Favorably, the drop is attached to the exits (or outlet ends) of four or more channels, or to a small horizontal plane the material of which features a surface tension which is substantially adhesive for the washing fluid. Even droplets of the afore-mentioned rather large size do not detach themselves through the effect of gravity alone when they hang from a plane with good wettability.

BRIEF DESCRIPTION OF THE DRAWINGS

FIG. 4a shows an embodiment of the dispenser with a dispensing micropump (46), a capillary (30) and capillary tip (31), which is surrounded by a first cone (32) with milled gas channels (35) and a second cone (33) to cover the channels (35). A pressure surge can be used to feed a gas into the ring duct (38) through the feed-in (34). The pressure surge continues through the channels (35) and detaches the drop of dispensing liquid which is not shown here. In this embodiment, the washing fluid can be pumped in by micropump (47) through a further feed-in (36), runs through the channel (37) to the horizontal plane (41) above capillary tip (31), the plane (41) being wettable to hold a drop (40) of washing fluid enclosing the dispenser tip (31). It goes without saying that more than one channel (37) can be foreseen in such a design. The size of the drop of washing fluid is monitored photometrically and regulated by a device comprising a light source (43) and a light detector (44), whereby the light beam (45) casts a shadow of the drop (40) of washing fluid onto the light detector (44).

FIG. 4b depicts a similar embodiment, however without the extra channel (37). The washing fluid, for instance ethyl alcohol or some other suitable pure liquid solvent, here is pumped in by micropump (48) through feed-in (39) into the gas channel system with at least four channels (35), preferably when the feed-in (34) for the gas is closed. In this case, the horizontal plane (42) is not required to be wettable, if the substantial contact of the drop (40) of washing fluid with the washing fluid in the channels (35) is sufficient for a hold. Also in this FIG. 4b, the drop (40) is fully enclosing the dispenser tip (31). The drop (40) solely hangs from the exits (or outlet ends) of the at least four channels (35) and is monitored and regulated photometrically by the device comprising light source (43) and light detector (44). After cleaning the dispenser tip by alternatingly drawing in into the central capillary (30) and pressing out again some of the washing fluid with the dispensing micropump (46), a surge of gas or pumping some more washing fluid removes the drop (40) of washing fluid, and, by reversing the pumping direction of the micropump (48) for the washing fluid, the gas channels (35) are dried by air to remove residual solvent. The air sucked in in this way dries the inner walls of the gas channels (35) in a rather short time of about one to five minutes.

FIG. 5 depicts a typical calibration curve, as is obtained with a syringe piston pump, creating spherical drops of known volume hanging at the tip of the dispenser. The relationship between the detector signal strength (here in volts) and the drop volume is stable up to a volume of 4 to 5 microliters and can be used for regulation of the drops of dispensing liquid, particularly well for smaller drops up to about 3 microliters. For measuring the larger drops of washing fluid up to eight or ten microliters, hanging from the horizontal plane and enclosing the tip, an independent calibration curve has to be created and used, since portions of the drop of washing fluid are attached around the outer circumference of the central dispensing capillary thereby being blocked from a field of view of the light detector (whereas a drop of dispensing liquid hanging only from the tip of the dispensing capillary is exposed to the light from the light source with virtually its entire volume). The calibration curve for drops of washing fluid should, however, have a similar form in that the amount of light received by the detector declines monotonically with increasing drop size.

DETAILED DESCRIPTION

Dispensers for the microliter range usually detach a drop of dispensing liquid by mechanical, acoustic, shock wave, or hydromechanical means to make it fall vertically onto the sample support. During dispensing of hundreds of samples, solved material may crystallize over time as deposit at the capillary tip of the dispenser, which impedes the vertical detachment of the drop of dispensing liquid in the medium and long run. Therefore, frequently cleaning the capillary tip is essential for a robust operation of the preparation device. The invention proposes to clean the dispenser tip by creating a drop of washing fluid through a channel outside the central dispensing capillary so that it completely encloses the dispenser tip. The size of the hanging drop of washing fluid is photometrically monitored and regulated to prevent the drop of washing fluid from falling off prematurely. Alternatingly drawing in into the central dispensing capillary and pressing out again parts of the drop of washing fluid may help to clean the dispenser tip.

Any type of dispenser, dispensing drops in the microliter range, can be used as the basis of the invention. For example, a dispenser can be used, with which a drop of dispensing liquid is pressed out of a capillary tip and detached by any chosen process with controlled activation so that it falls vertically onto a sample site of a sample support. This process can, for example, be a pressure surge in the liquid, possibly caused by a piezo element or a bubble-producing heating element, or a pressure surge in a gas flow surrounding the drop. Moving the capillary upwards with a jerk can also detach the drop. The required droplets with a diameter of around 1.0 to 1.4 millimeters (equivalent to a volume of 0.5 to 1.5 microliters) do not detach themselves from a pipette tip or a capillary by the effect of gravity alone, even if the capillary tip is relatively thin and the force of the surface tension at the neck of the drop is rather small.

Figure 1:
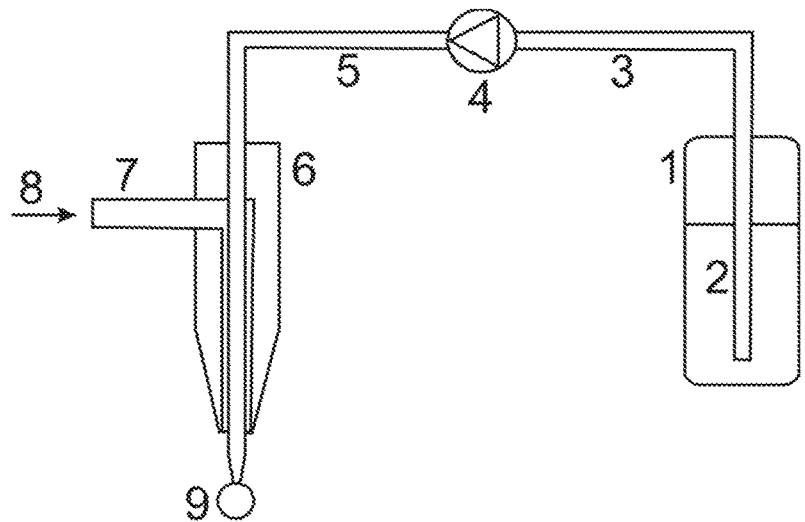
FIG. 1 depicts a simple dispenser design according to the prior art, the basic principles of which can also be used in conjunction with the present invention. A liquid (2) to be dispensed, such as a matrix solution for MALDI or a mixture of matrix and analyte sample, is aspirated from a vessel (1) via a tube (3) by a micropump (4) and is pressed through the tube (5) into a drop (9). When the drop (9) is the right size, it is detached from the tip of the tube (5) by a pressure surge of a gas (8) through the tube (7).

The dispenser shown in FIG. 1 is known in principle from the prior art, but can as such also be part of a dispenser system according to the invention. It operates as follows: the drop (9) of dispensing liquid which is pressed out of the inner capillary (5) by the micropump (4) is detached, in this case without contact, by a pressure surge (8) of a gas flow from a capillary (7) surrounding concentrically the inner capillary (5).

The operation of such dispensers regularly suffers from the formation of deposits at the tip of the dispensing capillary when solutions near saturation have to be used. Material easily crystallizes at the tip and hampers correct function. Quite often a mushy mixture of microcrystals with liquid forms a thick paste, creeping up at the outside at one side of the tip. Then, the drops of dispensing liquid do no longer hang symmetrically from the tip, but are drawn to one side by the deposit. Thereby the danger arises that the detached drops of dispensing liquid do no longer fall strictly vertically, and eventually fail to hit the correct sample site.

Because the sometimes gel-like deposits creep up the outside of the tip during continuing dispensing operation, the tip should be freely protruding from any hold by a few millimeters, so that the hold of the tip cannot be contaminated. In particular, the tip should not be surrounded by a narrow tube with a gap being formed in between (for instance, to guide the gas surge), because a deposit within the gap between tip and tube is hard to remove and requires much longer cleaning processes.

The invention is intended for repeatedly cleaning the pipette tip of the dispenser by fast cleaning processes, either periodically or after detection of deposits. By software control, automatic cleaning is possible without any help from the operator. The invention provides devices and automatic methods for cleaning dispensers without having to dismount the dispenser or even to remove the dispensing liquid from the dispenser capillary. The cleaning process can be started any time, for instance periodically, or each time after the preparation of all samples of a support plate with a certain number of samples, such as 384, or after the detection of deposits at the tip of the capillary.

In contrast to time-consuming and solvent-consuming cleaning processes known in the prior art, the cleaning according to the invention only needs a short time and a tiny amount of washing fluid. The invention proposes to feed the washing fluid for dissolving the deposit not through the inner capillary of the dispenser, but through one or more outer channels to the outside of the tip of the capillary, where the deposit is located in most cases, so that a drop of washing fluid (40) can be created which completely encloses the outside of the dispenser tip (31). Favorably, the washing fluid is fed to a location a little distance above the dispenser tip, for example amounting to about one to two millimeters, just where the cone of the tip (31) ends. For instance, as shown in FIG. 4b, one or all of the at least four gas channels (35) may be used to create this drop (40) of washing fluid enclosing the tip (31) of the dispensing capillary. In this case, the drop (40) may hang from the fluid inside the exits (or outlet ends) of the at least four gas channels (35) ending in the plane (42). On the other hand, it is possible to use an extra channel (37), or several extra channels, which ends in a plane (41) near the tip (31) of the inner capillary, to form the drop (40) of washing fluid, as shown in FIG. 4a. If only a single channel is used, as in FIG. 4a, the plane (41) is preferably configured to be substantially wettable in order to hold the drop (40). The drop (40) of washing fluid enclosing the tip (31) of the dispenser makes it possible to carry out the cleaning without having to change the dispensing liquid in the inner dispensing capillary (30), which accelerates and facilitates the cleaning process in general.

To make the drop of washing fluid fully enclose the dispenser tip, the channels (35, 37) may end in a wettable horizontal plane (41) at which the drop (40) can adhere. A material providing adhesive properties for washing fluids would be a metal, such as stainless steel or aluminum; as the case may be, a metal layer could be applied to a suitable substrate by some evaporation process. By this means the drop (40) of washing fluid can fully enclose the dispenser tip (31) even if the outer wall of the tip has a surface tension which does not allow to easily wet the surface by the washing fluid. This is the case for commercial dispenser tips made from polytetrafluoroethylene (PTFE) which is unwettable by most solvents. PTFE is the preferred material for the inner capillary (30) because it is chemically very inert.

As already mentioned, the fluid within the exits of the at least four gas channels (35) may hold the larger washing drop (40) even if the plane (42) is not particularly wettable. However, also the plane (42) from FIG. 4b could comprise an easily wettable material.

The washing fluid can be pumped to the dispenser tip (31) by a further micropump (47 or 48) to form the drop (40). Preferably a pure liquid solvent, e.g. ethyl alcohol, may serve as washing fluid, capable to solve the crystalline deposit. It has been found advantageous to form a relatively large drop of solvent on the capillary tip (31), with a volume of around 4 to 8 microliters, controlled and regulated by an optical drop size measuring unit comprising a light source (43) and a light detector (44). After forming the drop (40) of washing fluid through the outer channel(s) (35 or 37), it is kept motionless for about 30 seconds to soak the deposits at the outside of the tip. Subsequently, the drop (40) of washing fluid is brought in motion for another 30 seconds by drawing a part of the washing fluid from the drop into the capillary tip (31) and pressing it out again with the dispensing micropump (46), again photometrically monitored and controlled. As dispensing micropump (46), either a motorized syringe piston pump may be used or, much less expensive, a small peristaltic pump, in which a tube is pressed together in a bed by moving rollers. This motion of the drop (40) of washing fluid dissolves the deposits, particularly also in the inner part of the tip (31). The drop (40) of washing fluid can then be dropped into a waste shaft (not shown) by a pressure surge or by an increase of the drop size, that is, more washing fluid is supplied through the outer channel(s) (35, 37) until the detachment threshold due to gravity is exceeded. Subsequently, a new drop (40) of washing fluid may be formed in order that the washing cycle is repeated with clean washing fluid. Finally, the drop (40) of washing fluid may be removed by a gas surge. By changing the pumping direction of the washing fluid micropump (48), first the residual washing fluid and then air is drawn in to dry the gas channels (35), needing about one to five minutes for example. A full cleaning process may consist of three to ten washing cycles, each with a new drop (40) of washing fluid. If required, this washing process can be repeated several times, but in general it has been found that the process is very efficient so that a single cleaning process may be sufficient.

Even if three to ten drops (40) are used in subsequent cycles of the cleaning process to clean the tip (31) of the capillary, less than 100 to 200 microliters washing fluid is consumed in a single cleaning process. With a bottle of about 200 milliliters of washing fluid, 1000 to 2000 cleaning processes can be performed, each taking a few minutes only.

The generation of the rather large drop (40) of washing fluid and the motion of the drop by drawing in and pressing out some of the drop fluid endangers the hold of the drop; the drop (40) of washing fluid may fall off prematurely, particularly if inexpensive peristaltic pumps are used which do not work smoothly. Therefore, the invention is particularly applicable for contactless dispensers comprising an optical device with light source (43) and light detector (44) to monitor and regulate the size of each individual hanging drop (40) before it is detached, as shown schematically in FIG. 3. With these devices, it is not only possible to monitor and regulate the drop (9) of dispensing liquid (FIG. 3), but also the drop (40) of washing fluid (FIGS. 4a and 4b), using an extra calibration curve which, however, will bear some resemblance to the calibration curve of the drop of dispensing liquid as it will show a monotonic decline with increasing size of the drop.

The quantities of liquid to be dispensed onto the sample sites regularly amount to only 0.5 to 1.5 microliters, and form droplets around 1.0 to 1.4 millimeters in diameter. For the washing process, a drop volume of 4 to 8 microliters has proven to be favorable, with a diameter of about 2.0 to 2.7 millimeters, enclosing the dispenser tip. Droplets of this size are in danger of falling off prematurely by irregularities of the pumping speed of peristaltic pumps or other irregularities. Increasing the drop of washing fluid to about 10 to 20 microliters lets the drop fall, due to the gravity force, wherein the precise volume is depending on the surface tension at the drop's neck.

For monitoring and regulating the size of the drops, a photometric device may be used, as schematically shown in FIGS. 4a and 4b. Although the drops are usually quite transparent, the light beam from a light source, which is guided past the capillary tip of the dispenser, casts a clearly visible shadow of the generally round drop onto the detector because the light incident on the drop is strongly focused by the large difference in the refractive index between air and liquid (see FIG. 2). The light falling onto the drop is so divergent beyond the near focal point that it contributes almost nothing to the amount of light at the location of the detector, given suitable spacing between light source, drop and detector. The shadow reduces the amount of light on the detector and the resulting signal strength can thus be used to regulate the drop size for dispensing or washing. It is preferable if the diameter of the detector is greater than the shadow cast by the largest drop, whose size is still to be regulated.

When evaluating the amount of light on the detector in the presence of a drop at or around the dispenser tip, the rather irregular dimensions of a drop of washing fluid, pendant from a point slightly set back from the tip of the dispensing capillary, compared to the rather regular spherical shape of a drop of dispensing liquid, pendant directly and only from the quite sharp capillary tip, will have to be accounted for. For instance, as indicated in FIGS. 4a and 4b the drop (40) of washing fluid is not strictly spherical but has a round convex portion extending beyond the tip of the dispensing capillary (31) and actually being exposed to the light beam (45) from a light source (43). The optical imaging properties of this convex portion, such as the focal length, differ quantitatively but not necessarily qualitatively from those of a spherical drop used for the explanation of the basic principles of photometric monitoring and regulation that follows.

Figure 2:
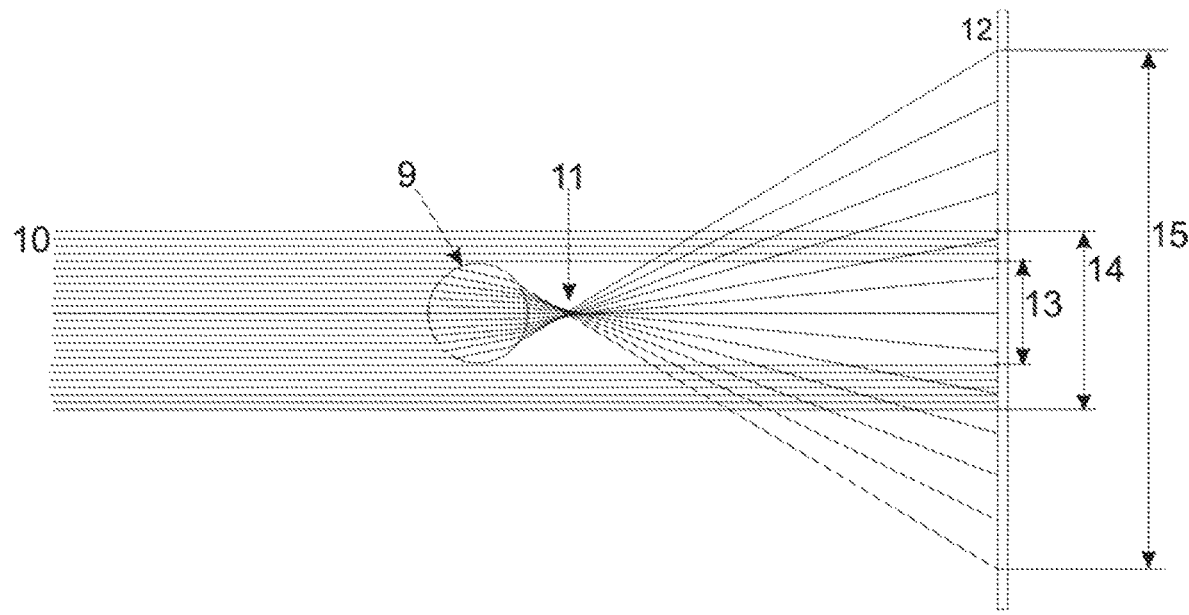
FIG. 2 shows the shadow cast by a spherical drop (9) in a parallel beam of light (10), for example a laser beam or other suitable collimated beam. The drop generates a focus (11), and the divergent light from the focus is imaged in the detector plane (12) onto an area with a large diameter (15). If the distance between drop and detector is chosen favorably, the shadow (13) in the original light spot (14) of the parallel beam is illuminated only by a small amount of light from the focus, and thus a marked brightness contrast is produced between the area of shadow (13) and the outer original light spot (14).

As can be seen in FIG. 2, a spherical drop (9) forms a clearly visible shadow in a parallel beam (10), although from a strictly physical point of view, a shadow is only defined for a body made from a non-transparent medium. It would be scientifically more correct to talk about a difference in contrast, but the term "shadow" will be used continuously in the following for the sake of clarity. The shadow forms as a result of the optical deflection of the light which falls onto the drop, due to the refractive power of the drop. The light incident on the drop is focused with a short focal length by the lens effect of the drop. Beyond the near focal point (11), the light is so divergent that it hardly lightens the cast shadow (13) if the distance between the drop (9) and the detector (12) is suitably chosen. If the detector area (not shown here) in the detector plane is only slightly larger than the shadow cast by the largest drop to be regulated, for example with a detector diameter as large as the diameter (14) of the light beam, the amount of light which falls onto the detector can be used to monitor and regulate the drop size and, in particular, to determine the moment at which the drop is about to be detached from the dispenser tip.

The relationship between the light signal of the detector and the volume of the drop must be determined by calibrations. FIG. 5 presents a calibration curve for spherical drops freely hanging on the dispenser tip. The calibration can be carried out very easily with an accurate syringe piston pump. Up to a volume of four to five microliters, a stable and reproducible signal is obtained, which is very well suited for the regulation. For drops of washing fluid, for instance hanging from a substantially wettable plane, fully enclosing the dispenser tip and thereby having a rather irregular shape, a separate calibration has to be performed that accounts for the fact that a focal length, or in other words the light transmission properties of the drop, cannot be as easily defined as in the case of a spherical drop. It has been found, however, that, once a proper calibration is established, both types of calibration can be transferred within the required accuracy to regulating systems of the same design.

Monitoring and regulating the size of a drop (40) of washing fluid may be performed as follows: once a cleaning cycle is initiated, an amount of light emitted from the light source (43) and received by the light detector (44), which in favorable embodiments can be located at a position diametrically opposite to the position of the light source (43) in relation to a dispenser axis (not shown), is evaluated as to which amount of washing fluid is currently attached at and around the tip (31) of the dispensing capillary. If the detected amount is not sufficient for the drop of washing fluid fully enclosing the capillary tip, a command signal is issued to the micropump (47, 48) for supplying the washing fluid that more washing fluid has to be delivered. The micropump (47, 48) will then pump more washing fluid through the outer channel(s) (35, 37) to the capillary tip (31) and, after a predetermined period of pump operation, a further light detector reading will be made. If a minimum threshold of drop size, which indicates that the size of the drop of washing fluid is sufficient for enclosing the capillary tip in its entirety, is exceeded the micropump will receive a command signal to stop operation and the drop of washing fluid will be kept hanging at and around the capillary tip for a predetermined period of time, such as about several seconds up to minutes, so that deposit dissolving can take effect. Then, the drop of washing fluid can be disposed into waste, which requires that the dispenser device and a waste shaft have been brought into alignment beforehand.

Optionally, after a first period of "passive" dissolving in which the drop (40) of washing fluid just hangs at and around the capillary tip (31), in a second period of "active" dissolving, parts of the drop (40) of washing fluid may, alternatingly, be drawn into the capillary tip and pressed out again, as the case may be repeatedly, by correspondingly back and forth operating the dispensing micropump (46) for the central capillary (30). In particular during this second period of active dissolving, further light detector readings are made to avoid that the size of the drop of washing fluid exceeds a maximum threshold of drop size, which indicates that the size of the drop (40) of washing fluid approaches the critical size at which detachment due to gravity pull would occur, in a phase of pressing out. If the maximum threshold is reached, the dispensing micropump (46) receives a command signal to either start a period of reverse operation to draw in the drop of washing fluid into the capillary tip again or to stop further operation and, if a predetermined period of active dissolving, such as between several seconds up to minutes, has finished, the washing micropump (47, 48) receives a command signal to start an operation of disposing the drop of washing fluid into waste, as the case may be jointly with the micropump (46) for the dispensing liquid.

Due to the irregular dimensions of the drops of washing fluid (rather pear-shaped than spherical), the aforementioned minimum and maximum thresholds are preferably determined empirically and may correspond to certain voltage values, as shown in FIG. 5 on the y axis, if a photoelectric cell is used as light detector, for instance.

The light source and the light detector are preferably arranged and aligned such that the tip of the capillary slightly projects into the light beam. It is then possible, with this device, to recognize deposits on the capillary tip of the dispenser, for example by monitoring a base signal of light which is present when no liquid is being pressed out of the capillary tip (and even the meniscus is retracted), or by monitoring stray light with a second photoelectric cell or other suitable light detector. The second photoelectric cell or light detector is preferably located at a position off the axis of the light beam from the light source. Deposits on the capillary tip of the dispenser caused by crystallizing material can be detected in this way. Detection of a deposit can trigger an automatic cleaning of the dispenser capillary, in some cases even during a deposition sequence to ensure the reliable spotting of drops of dispensing liquid.

In an embodiment with a parallel light beam according to FIG. 2, the shadow of the drop, which has no penumbra here, can be produced using a light beam from a laser diode or a small laser. Since the beams from relatively low-cost laser diodes or small lasers have only small diameters, the laser beam must be expanded by a telescope-like lens system to a diameter which is larger than the drop.

Figure 3:
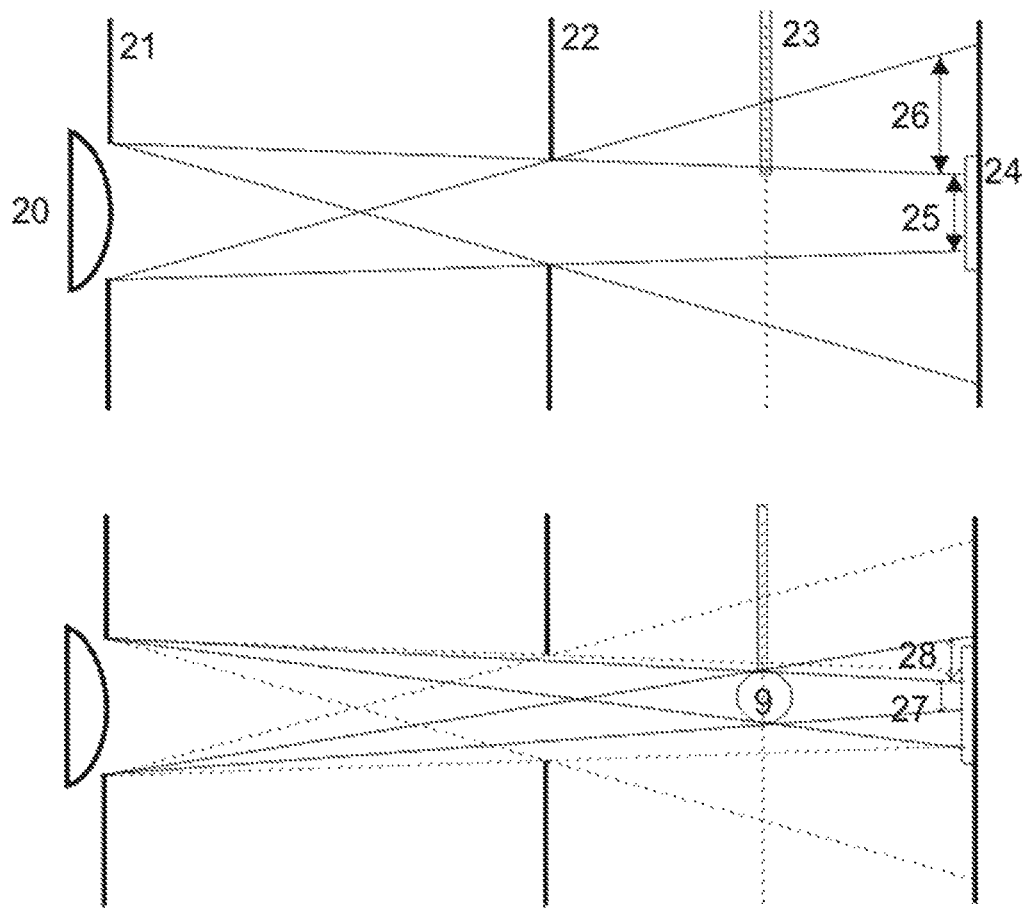
FIG. 3 shows the beam path of the light from a relatively large surface area of a light-emitting diode (20) without a drop (top) and with a spherical drop (9) (bottom). Two apertures (21) and (22) form a light beam, which generates a circle of full light (25) with an aperture penumbra (26) in the plane of the detector (24). As can be seen in the lower figure, a drop (9) on the capillary (23) forms an umbra (27) with surrounding drop penumbra (28). Here too, the light which passes through the drop (not shown here) is so divergent that it makes almost no contribution to the amount of light on the detector (24). The amount of light on the detector (24) can therefore be used to regulate the drop size or to determine the moment at which the growing drop is detached from the capillary tip.
Figure 6:
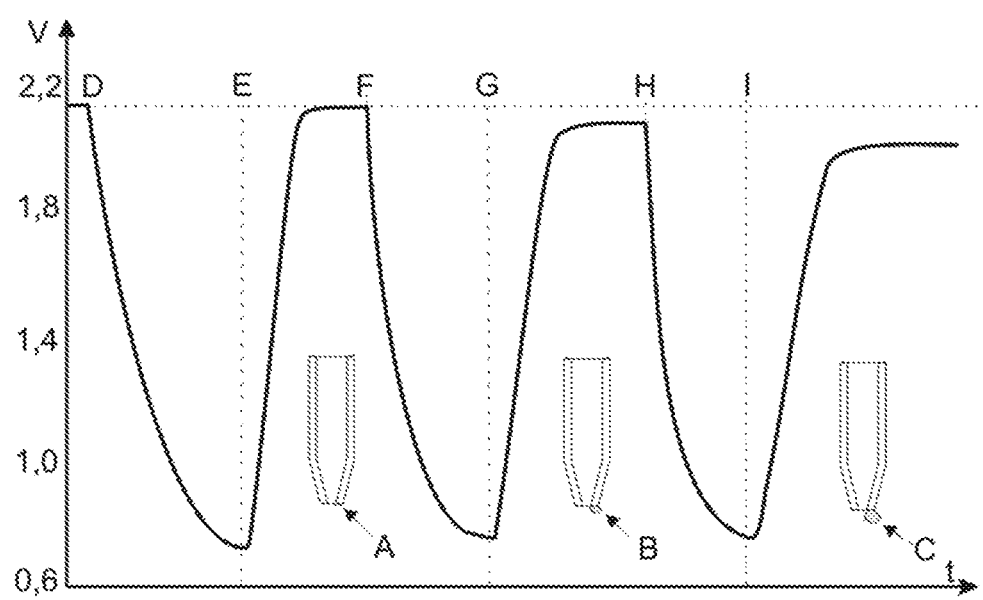
FIG. 6 shows how deposits on the capillary tip of the dispenser can be measured by virtue of the fact that, due to the shadow cast by the deposits when no droplet of whatever kind is pendant from or at the capillary tip, the signal strength at the detector does not return to the original value (broken horizontal line) which it has for a clean capillary (A). Depending on the size of the deposits (B) and (C), there remains a smaller or larger difference from the original signal strength. At the times (D), (F) and (H), the micropump starts to press the drop of dispensing liquid from the dispensing capillary; at the times (E), (G) and (I), the drop of dispensing liquid is detached and the micropump may be stopped.

In the embodiment according to FIG. 3, an optical device with an extended light source (20) and a light detector (24) can be seen. A light beam from the surface area of a light source (24), limited by the apertures (21) and (22), casts an umbra (27) of the spherical drop with surrounding penumbra (28) of the drop onto the detector; here also, it is possible to use the residual light on the detector to regulate the drop size. Here too, the light, which is focused by the spherical form of the drop (9) (not shown in FIG. 3 for reasons of clarity), becomes so divergent beyond the focal point that it makes hardly any contribution to the amount of light on the detector (24) if the spacings at the location of the detector are chosen appropriately.

The light beam can be generated by laser diodes, but preferably by simple and more economic light-emitting diodes (LEDs) of sufficient luminosity, and can be formed or restricted by lenses, but preferably by simple apertures, in such a way that a sufficiently large umbra of the drop is generated. The light detector can preferably be a photoelectric cell or charge-coupled device (CCD). The arrangement of FIG. 3 depicts the forming of the light beam by simple apertures.

For a preferred embodiment according to FIG. 3, a simple and very low-cost light-emitting diode (LED) of sufficient size and luminance can be used as the light source (20), with a power supply which is also low-cost. The light beam of a sufficiently bright light-emitting diode (20) is simply restricted by two apertures (21) and (22) here in order to provide proper collimation, and forms a low-cost system that is simple and stable with regard to accurate positioning, and generates an umbra (27) and a surrounding penumbra (28) from the drop.

As has been noted above, it is preferable here to detach the drop of dispensing liquid by a pressure surge of a gas blowing against it. It is, however, not easy to keep two capillaries (5) and (8), the inner one for forming the drop of dispensing liquid, the outer one for the detaching gas surge, exactly coaxial, as shown in FIG. 1. Even a slight deviation may have the effect that the drop (9) is no longer detached vertically. For this reason, devices as shown in FIGS. 4a and 4b are preferred. Here, a cone (32) which closely surrounds the droplet capillary (30) has at least two, preferably four or more, outer channels (35) covered by the cone (33), which direct the gas surge towards a drop of dispensing liquid (which is not the drop (40) of washing fluid shown in these figures) at the tip (31) of the dispensing capillary (30) and force it to fall off by abruptly exerting a gas pulse against it. The pressure surge can be generated by a tiny piston pump, for example, and fed to the admission aperture (34). The piston pump can consist of a simple piston in a cylinder, where the piston is moved by a simple electromagnet and reset by a spring so that the cylinder can be filled and emptied. The resetting by the spring could then generate the pressure surge.

If deposits have to be removed, the dispenser capillary can be cleaned automatically. For each washing cycle of the simple cleaning process, a second micropump (47, 48), preferentially a low-cost peristaltic pump, feeds the solvent as the washing fluid for dissolving the deposit, as is shown in FIG. 4a, not through the inner capillary (30), but through an outer channel, for example through an additional milled channel (37) in the above-mentioned cone (32), which closely surrounds the inner capillary (30). Instead, one or all of the gas channels (35) may be used to feed the washing fluid to the tip (31) of the dispensing capillary, as shown in FIG. 4b. If the tip protrudes from a flat horizontal plane (41) with good wettability, such as by about one or two millimeters, the drop (40) of washing fluid will hang down from this flat area and fully enclose the dispenser tip. The size of the drop (40) of washing fluid is monitored by the photometric device (43, 44). This external feeding process makes it possible to carry out the cleaning without having to change the dispensing liquid in the inner capillary (30), which accelerates the process in general. The cleaning can be supported by a motion of the drop (40) of washing fluid, caused by alternatingly drawing into the inner capillary (30) and pressing out again some of the drop (40) of washing fluid by the dispensing micropump (46). Also in this period the drop of washing fluid is monitored and controlled by the photometric device in order that, during the pressing-out phase, the drop (40) of washing fluid does not grow too large as a consequence of which it would be unintentionally falling off from the tip (31) prematurely due to the gravity pull. After a washing cycle, the drop (40) of washing fluid is detached by pumping some more washing fluid into it. At the end of the cleaning process, after a predetermined number of washing cycles, such as three to ten, the washing fluid can be removed by a gas surge through the gas channels, and the washing channels can be dried by fast sucking air by the washing micropump (48) for about one to five minutes.

The cleaning systems can be beneficially used to switch the whole dispenser system into a standby state when sample support plates have to be exchanged, or when the whole system should be switched down for a short period. An amount of liquid corresponding to one or more drops of washing fluid may be sucked into the dispensing capillary, either in direct contact with the dispensing fluid, or even with an air bubble in between by first sucking a bit of air into the dispensing capillary. This measure of closing the capillary with some washing fluid serves to keep the tip of the dispenser from being contaminated by crystallizing material. The standby state can thus be kept for hours or even days without having to empty the dispenser capillary. After switching on again, the washing fluid and some of the dispensing fluid is dripped into waste, to bring fresh and undiluted (and unpolluted) dispensing liquid to the tip.

This cleaning system has several advantages: cleaning can be performed automatically without manual intervention; the cleaning process is highly timesaving; a stand-by mode without the danger of crystallization is possible; furthermore, the consumption of washing fluid is very low (a bottle with 200 milliliters ethyl alcohol may serve for 1000 to 2000 cleaning processes, for instance).

Several dispenser systems, either with individual monitoring and regulating device for the drop size, or with a common photometric measuring device for all dispensers, can be used to prepare the samples with several different dispensing liquids. Dispenser systems with cleaning devices according to the principles of the invention are particularly advantageous when working with dispensing solutions, particularly with solutions near saturation which are particularly prone to crystallization of deposits.

The invention has been shown and described with reference to a number of different embodiments thereof. It will be understood, however, that various aspects or details of the invention may be changed, or various aspects or details of different embodiments may be arbitrarily combined if practicable, without departing from the scope of the invention. Furthermore, the foregoing description is for the purpose of illustration only, and not for the purpose of limiting the invention, which is defined solely by the appended claims.

The invention claimed is:

1. A method for cleaning a tip of a dispensing capillary, wherein a washing fluid is fed through at least one outer channel to a location slightly set back from the tip of the central dispensing capillary to form a drop fully enclosing the tip, wherein the size of the drop is monitored and regulated photometrically by a device having a light source and a light detector to prevent the drop of washing fluid from falling off before deposit dissolving can take effect.

2. The method according to claim 1, wherein the drop of washing fluid is formed at a horizontal plane being wettable by the washing fluid so that the drop can fully enclose the tip even if a tip material is unwettable by the washing fluid.

3. The method according to claim 1, wherein the drop of washing fluid is kept in motion by at least once drawing it partly into the dispensing capillary and pressing it out again with the aid of a dispensing micropump used to dispense liquids through the dispensing capillary.

4. The method according to claim 1, wherein an amount of light received by the light detector in a phase where no drop is pendant from an end of the at least one outer channel is used to detect deposits at the tip of the dispensing capillary.

5. The method according to claim 1, wherein some washing fluid is drawn into the dispensing capillary to protect the tip from being contaminated with crystallizing material during standby times.

6. The method according to claim 1, wherein, in certain phases of operation, a first micropump presses a drop of dispensing liquid out of the tip of the dispensing capillary and a detachment device detaches the drop of dispensing liquid from the tip of the dispensing capillary, and wherein, in alternate phases of operation, a second micropump presses the washing fluid through the at least one outer channel outside of the dispensing capillary to form the drop of washing fluid hanging from the end of the at least one outer channel and fully enclosing the dispensing capillary tip.

7. The method according to claim 6, wherein the detachment device for dispensing a drop from the tip of the dispensing capillary comprises one of a device to generate a pressure surge of a gas, a device for jerky detachment, a piezo device, and a vapor-bubble generator.

8. The method according to claim 6, wherein at least one of the first micropump and the second micropump is a peristaltic micropump or a piston pump.

9. The method according to claim 1, wherein the at least one outer channel ends in a flat horizontal plane a material of which is configured such that it has adhesive properties for being wettable by the washing fluid, in order to enable the drop of washing fluid to fully enclose the dispenser tip even if a material of the dispenser tip is unwettable by the washing fluid.

10. The method according to claim 9, wherein the material of the flat horizontal plane comprises metal.

11. The method according to claim 1, wherein the material of the dispensing capillary comprises polytetrafluoroethylene (PTFE).

12. The method according to claim 1, wherein the tip of the dispensing capillary projects into the light beam between light source and light detector to photometrically detect deposits when no drop is pendant from the capillary tip.

13. The method according to claim 1, wherein the light source and the light detector are located diametrically across a dispensing capillary axis.

14. The method according to claim 1, wherein the light source is one of a light-emitting diode (LED), a laser and a laser diode and comprises lenses or apertures as light-beam forming elements.

15. The method according to claim 1, wherein the light detector is one of a photo-electric cell and a charge-coupled device (CCD).

16. The method according to claim 1, wherein at least one of the first micropump and second micropump perform an oscillatory backward and forward pumping of liquid.

17. The method according to claim 1, wherein the at least one outer channel comprises one of an extra channel for supplying washing fluid and a gas channel for exerting gas pulses on drops hanging from, or at, the tip of the dispensing capillary.

18. The method according to claim 1, wherein the at least one outer channel for supplying washing fluid comprises two or more channels being arranged in a rotationally symmetric manner around the dispensing capillary.

19. The method according to claim 1, wherein a volume of the drop of washing fluid amounts to between about four and eight microliters.

\* \* \* \* \*